(12) United States Patent
Kasahara

(10) Patent No.: US 8,409,115 B2
(45) Date of Patent: Apr. 2, 2013

(54) BODY COMPOSITION MEASURING APPARATUS

(75) Inventor: Yasuhiro Kasahara, Tokyo (JP)

(73) Assignee: Tanita Corporation, Tokyo (JP)

( * ) Notice: Subject to any disclaimer, the term of this patent is extended or adjusted under 35 U.S.C. 154(b) by 425 days.

(21) Appl. No.: 12/175,286

(22) Filed: Jul. 17, 2008

(65) Prior Publication Data
US 2009/0024053 A1 Jan. 22, 2009

(30) Foreign Application Priority Data
Jul. 19, 2007 (JP) .................. 2007-187764

(51) Int. Cl.
*A61B 5/103* (2006.01)
*A61B 5/117* (2006.01)
*A61B 5/05* (2006.01)

(52) U.S. Cl. ........................... 600/587; 600/547
(58) Field of Classification Search ............ 600/547, 600/587
See application file for complete search history.

(56) References Cited

U.S. PATENT DOCUMENTS

| | | | | |
|---|---|---|---|---|
| 4,406,544 A * | 9/1983 | Takada et al. | ................ | 356/612 |
| 5,415,176 A * | 5/1995 | Sato et al. | ................ | 600/547 |
| 5,850,290 A * | 12/1998 | Horiguchi et al. | ........... | 356/602 |
| 6,327,494 B1 * | 12/2001 | Sakai | ........................ | 600/547 |
| 7,957,795 B2 * | 6/2011 | Tsuji | ........................... | 600/547 |
| 2001/0030754 A1 | 10/2001 | Spina et al. | | |
| 2005/0101884 A1 * | 5/2005 | Weeks et al. | ................ | 600/587 |
| 2005/0209528 A1 * | 9/2005 | Sato et al. | .................... | 600/547 |
| 2008/0021349 A1 * | 1/2008 | Sakai et al. | .................. | 600/587 |
| 2009/0182243 A1 * | 7/2009 | Oku et al. | ..................... | 600/547 |

FOREIGN PATENT DOCUMENTS

| | | |
|---|---|---|
| EP | 02/065900 A2 | 8/2002 |
| EP | 1 882 447 A1 | 1/2008 |
| EP | 1 882 448 A1 | 1/2008 |
| EP | 1 967 136 A1 | 9/2008 |
| JP | 2001212111 A | 8/2001 |
| JP | 2002024987 A | 1/2002 |
| JP | 2002-85365 A | 3/2002 |
| JP | 2002159461 A | 6/2002 |
| JP | 2003093363 A | 4/2003 |
| WO | 02/065900 A2 | 8/2002 |
| WO | WO 2007063631 A1 * | 6/2007 |

OTHER PUBLICATIONS

European Search Report rec'd in corresponding EP Appl. No. 08011909 dated Oct. 31, 2008.
Japanese Office Action (Application No. 2007-187764) Issued Apr. 10, 2012.

* cited by examiner

Primary Examiner — Sean P Dougherty
Assistant Examiner — Devin Henson
(74) Attorney, Agent, or Firm — Hogan Lovells US LLP

(57) ABSTRACT

A CPU (134) of a body composition measuring apparatus (100) drives a navel position indicator (118) so that it emits light. The height of a frame (114) is adjusted so that a beam of light from navel position indicator (118) irradiates the navel of a human subject. Plural sensors (106) are mounted on the frame (114), and each sensor measures a distance from the sensor to a position to be measured, whereby the abdominal width (X) of the human subject is determined. Subsequently, CPU (134) obtains measured values of weight (W) and bioelectrical impedance (Z). CPU (134) then reads an equation for calculating the visceral fat area and estimates the visceral fat area (Y) based on the measured abdominal width (X), weight (W), bioelectrical impedance (Z), and the equation.

18 Claims, 6 Drawing Sheets

BODY COMPOSITION MEASURING APPARATUS

BACKGROUND OF THE INVENTION

1. Field of the Invention

The present invention relates to a body composition measuring apparatus for measuring the abdominal size of a human subject and for calculating an index of body composition based on the measured abdominal size.

2. Description of Related Art

Abdominal size has been widely used as an index for evaluating the physiques of humans. Abdominal size may be used as an index reflecting conditions of the trunk of the body, such as the amount of visceral fat. For example, if a person A and a person B were of the same height, if person A were to have a larger abdominal size, person A would have a higher degree of obesity, whereas if person B were to have a smaller abdominal size, person B would have a lower degree of obesity. For this reason, abdominal size is an index that is receiving attention as potentially helping people to avoid lifestyle-related diseases and adult-onset diseases so as to maintain good health.

There is disclosed, for example in Japanese Patent Application Laid-Open Publication No. 2002-85365, a device capable of obtaining a body composition index based on abdominal size and other parameters after receiving data on abdominal size that is manually input.

However, in a case in which a human subject or an operator inputs information regarding the abdominal size, such as waist circumference, the human subject or the operator does not always know the precise value of the waist circumference of the human subject, and therefore, the accuracy of the estimation of a body composition index tends to be unsatisfactory. In a case in which the waist circumference is input after it is measured, a tape measure or a band-type measure is often used. However, it is difficult and troublesome to position the tape measure or band-type measure at a desirable height horizontally all the way around the waist, for example, at the level of navel. Because the tape measure or band-type measure may often be misaligned, the values of the waist circumference in a series of measurements will be variable, i.e., the waist circumference cannot be measured in a reproducible manner.

There are other conventional body composition measuring apparatuses that are capable of estimating a body composition index without the abdominal size having to be input. However, indices such as fat ratio of the trunk portion, total fat area of the abdomen, abdominal subcutaneous fat thickness, abdominal muscle thickness, abdominal subcutaneous fat area, and visceral fat area in particular are highly correlated with abdominal size. Therefore, it is highly preferable to use abdominal size to more precisely estimate a body composition index. The abdominal size includes abdominal width (abdominal width in a lateral direction of the body of a human) and abdominal length (abdominal width in an anteroposterior direction of the body of a human) in addition to the above-described waist circumference.

SUMMARY OF INVENTION

Accordingly, the present invention has as an object to provide a body composition measuring apparatus capable of readily and precisely measuring abdominal width and capable of estimating a body composition index with a high degree of accuracy.

In accordance with one aspect, the present invention provides a body composition measuring apparatus for estimating a body composition index, the apparatus having a bioelectrical impedance measurer (bioelectrical impedance measuring means) that measures foot-to-foot bioelectrical impedance by applying at least one electrode to the sole of each foot of a human subject, an abdominal width measurer (abdominal width measuring means) that measures the abdominal width of the human subject, a weigher (weighing means) that measures the body weight of the human subject, a calculator (calculation means) that calculates a body composition index with respect to the human subject based on the abdominal width, the weight, and the foot-to-foot bioelectrical impedance, and the abdominal width measurer uses a reflection-type contactless distance measuring sensor to measure the abdominal width, the contactless distance measuring sensor measuring a gap distance between a position of the sensor and a position of a point to be measured.

The body composition index includes the fat ratio of the trunk portion, the total fat area of the abdomen, the abdominal subcutaneous fat thickness, the abdominal muscle thickness, the abdominal subcutaneous fat area, and the visceral fat area, but it is not limited thereto. Body composition indices are highly correlated with abdominal size. According to the body composition measuring apparatus of the present invention, because the abdominal width is used to calculate (estimate) a body composition index, the body composition index can be estimated with a high degree of accuracy. In other words, the accuracy in the estimation is increased in comparison with a case in which the abdominal size is not used as a parameter in the estimation.

Furthermore, in a case in which a tape measure or a band-type measure is wrapped around the body of a human subject, the tape measure or the band-type measure is often misaligned, and as a result, the waist circumference cannot be measured in a reproducible manner. Also, the measured values are affected by the deformation of the anterior surface of the abdomen that is caused by respiration. However, in the present invention, because the contactless distance measuring sensor is used to measure the abdominal width, a highly precise value for the abdominal width can be obtained with a high degree of reproducibility. Therefore, according to the body composition measuring apparatus, the abdominal width can be accurately measured in a reproducible manner, and therefore, a body composition index can be obtained with a high degree of accuracy. Moreover, since there is no need to wrap a measuring instrument around the entire waist, the body composition measuring apparatus can be operated without difficulty.

In a preferred embodiment, the present invention may have a height inputter (height input means) that receives input of the height of the human subject, and the calculator uses the height received by the height inputter in addition to the abdominal width, the weight, and the foot-to-foot bioelectrical impedance to estimate the body composition index. The height of a subject is a parameter that is highly correlated with the physique of humans when used in combination with the weight of the subject. For a subject of a particular weight, the degree of obesity decreases as the height of the subject increases, whereas the degree of obesity increases as the height of the subject decreases. In this embodiment, with the use of height as a parameter for estimation, the body composition index can be estimated with a higher degree of accuracy.

In another preferred embodiment, the apparatus of the present invention may have an age inputter (age input means) that receives input of the age of the human subject, and the calculator may also serve as a body density estimator (body density estimation means) that estimates body density based on the abdominal width, the weight, and the foot-to-foot bioelectrical impedance, and the calculator may calculate the body composition index based on the abdominal width, the body density, and the age input by the age inputter. In the conventional body composition index estimation, a body mass index BMI (weight/height$^2$), age, and body fat ratio are used as parameters, in which both the height and the age must be input. However, in the present embodiment, since the body density is used to estimate a body composition index, the height need not be input, and accurate estimation is still possible.

In a preferred embodiment, the abdominal width measurer includes at least two contactless distance measuring sensors and a frame on which the contactless distance measuring sensors are arranged so that the at least two contactless distance measuring sensors are facing each other and are sandwiching the abdomen, with a straight line connecting the sensors being in parallel with a lateral direction of the abdomen (i.e., a width direction of the abdomen), and the two contactless distance measuring sensors measuring the gap distance at plural positions that are in parallel with an anteroposterior direction of the abdomen (i.e., a direction orthogonal to the lateral direction of the abdomen), and the abdominal width measurer may execute a predetermined calculation on plural gap distances measured at the plural positions to output a result of the calculation as the abdominal width.

In this embodiment, for example, two contactless distance measuring sensors may be disposed on the frame and be synchronously moved in the anteroposterior direction, with the straight line connecting the sensors maintaining a parallel position with the lateral direction of the abdomen while moving, so that the sensors measure gap distances at the plural positions. Alternatively, two contactless distance measuring sensors may be arranged so that the sensors move in the anteroposterior direction of the abdomen independently of each other to measure gap distances at plural positions. In another alternative, plural pairs of contactless distance measuring sensors may be fixedly arranged on the frame so as to cause each pair of sensors to measure gap distances at plural positions. In any of the above configurations, the abdominal width measurer may, as the predetermined calculation, obtain plural candidates for the abdominal width and may select, from among the candidate abdominal width values, the one having the maximum value for output as the abdominal width. Alternatively, the abdominal width measurer may, as the predetermined calculation, obtain coordinates constituting an outer rim of the abdomen based on the gap distances detected by the sensors, execute curved interpolation based on the coordinates, and determine two coordinates having a maximum distance therebetween in the lateral direction of the abdomen to output the maximum distance as the abdominal width. According to this embodiment, the abdominal width used as the basis for the calculation of the body composition index can be measured smoothly, precisely, and with easy operations. Therefore, the burden placed on a human subject and an operator can be reduced, and better reproducibility in measurement can also be achieved. It is to be noted that, in the present invention, an operator of the apparatus may be the same person as the human subject, or another person may operate the apparatus as an operator to take measurements of the human subject.

In still another preferred embodiment, one side of the frame may preferably be open so that the human subject can enter the interior area of the frame from the open side. According to this configuration, the frame having sensors can be disposed around the human subject so that the sensors are located at opposite sides of the human subject, and the measurement can be easily performed. Conversely, in a conventional method, a tape-type measuring instrument or a band-type measuring instrument is wrapped all the way around the circumference of the trunk of the body. Therefore, a human subject or an operator must perform the cumbersome operation of wrapping the measuring instrument around the body. However, in the present invention, since one side of the frame is open, the human subject simply enters the interior area of the frame, and therefore, easy and speedy measurement of the abdominal width can be performed.

Furthermore, the frame has a navel position indicator (navel position indicating means) that indicates the position of the navel of the human subject, the apparatus further has a rod for supporting the frame so that the frame can slide along a medial line of the standing human subject and has a frame level changer (frame level changing means) for changing a level (a vertical position) of the frame along the rod, and the frame level changer brings the frame to rest at a position at which the navel of the human subject is indicated by the navel position indicator, and the abdominal width measurer may measure the abdominal width when the frame is stopped. Because the navel position indicator is thus provided, the level of the frame can be readily adjusted at the height of the navel, and therefore, the abdominal width at a certain height based on the navel can be accurately obtained. Preferably, the navel position indicator is a light emitter attached to the frame, the light emitter emitting a beam of light. In a case in which the navel position indicator is a light emitter, the frame can be positioned with reference to the human subject so that the beam of light being emitted points to the navel. Moreover, because the apparatus has a rod for supporting the frame so that the frame can slide along a medial line of the standing human subject and a frame level changer for changing a level of the frame along the rod, the frame can be moved automatically and easily along a medial line of the human subject by the frame level changer.

BRIEF DESCRIPTION OF THE DRAWINGS

With reference to the accompanying drawings, various embodiments of the present invention will be described hereinafter. In the drawings.

DETAILED DESCRIPTION OF PREFERRED EMBODIMENTS

An embodiment of the present invention is a body composition measuring apparatus 100 provided with an abdominal width measurer (abdominal width measuring means). The abdominal width measurer measures the maximum distance in a lateral direction of the abdomen (hereinafter referred to as "abdominal width") of a human subject 10 who is in the standing position, the abdominal width passing through the navel of human subject 10. Body composition measuring apparatus 100 has a foot-to-foot bioelectrical impedance measurer (foot-to-foot bioelectrical impedance measuring means) (a bioelectrical impedance device 170, which will be described later) for measuring foot-to-foot bioelectrical impedance of a human subject 10 and a weigher (weighing means) (a weighing device 160, which will be described later) for measuring the body weight of human subject 10. Body composition measuring apparatus 100 obtains a body composition index based on the measured abdominal width, foot-to-foot bioelectrical impedance, and body weight. The body composition index includes, but is not limited to, fat ratio of the trunk portion, total fat area of the abdomen, abdominal subcutaneous fat thickness, abdominal muscle thickness, abdominal subcutaneous fat area, and visceral fat area. In this embodiment, description will be given of a case in which visceral fat area is estimated based on the abdominal width.

Figure 1:
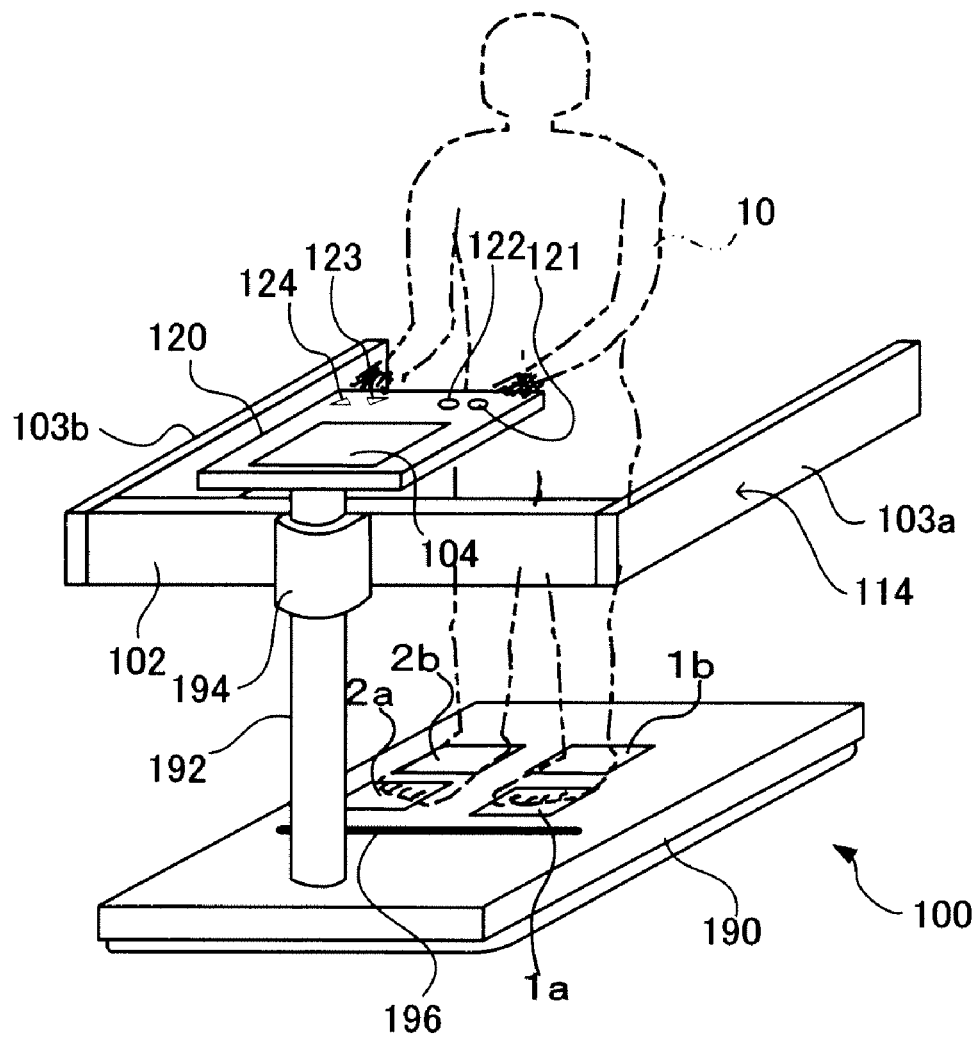
FIG. 1 is a perspective diagram showing an external view of a body composition measuring apparatus 100 according to an embodiment of the present invention.

In the following, description will be given of body composition measuring apparatus 100 of the embodiment with reference to FIGS. 1 to 7. FIG. 1 shows a perspective diagram showing an external view of body composition measuring apparatus 100 according to the present embodiment. As shown in FIG. 1, body composition measuring apparatus 100 is provided with a base plate unit 190 on which human subject 10 stands, a rod (or a pillar) 192 that stands upright vertically on base plate unit 190, and a frame (abdominal width measurer) 114 supported by rod 192 so that the frame can move in a vertical direction. On the top surface of base plate unit 190, there is drawn a reference line 196 along which the toes of human subject 10 should be aligned.

Figure 4:
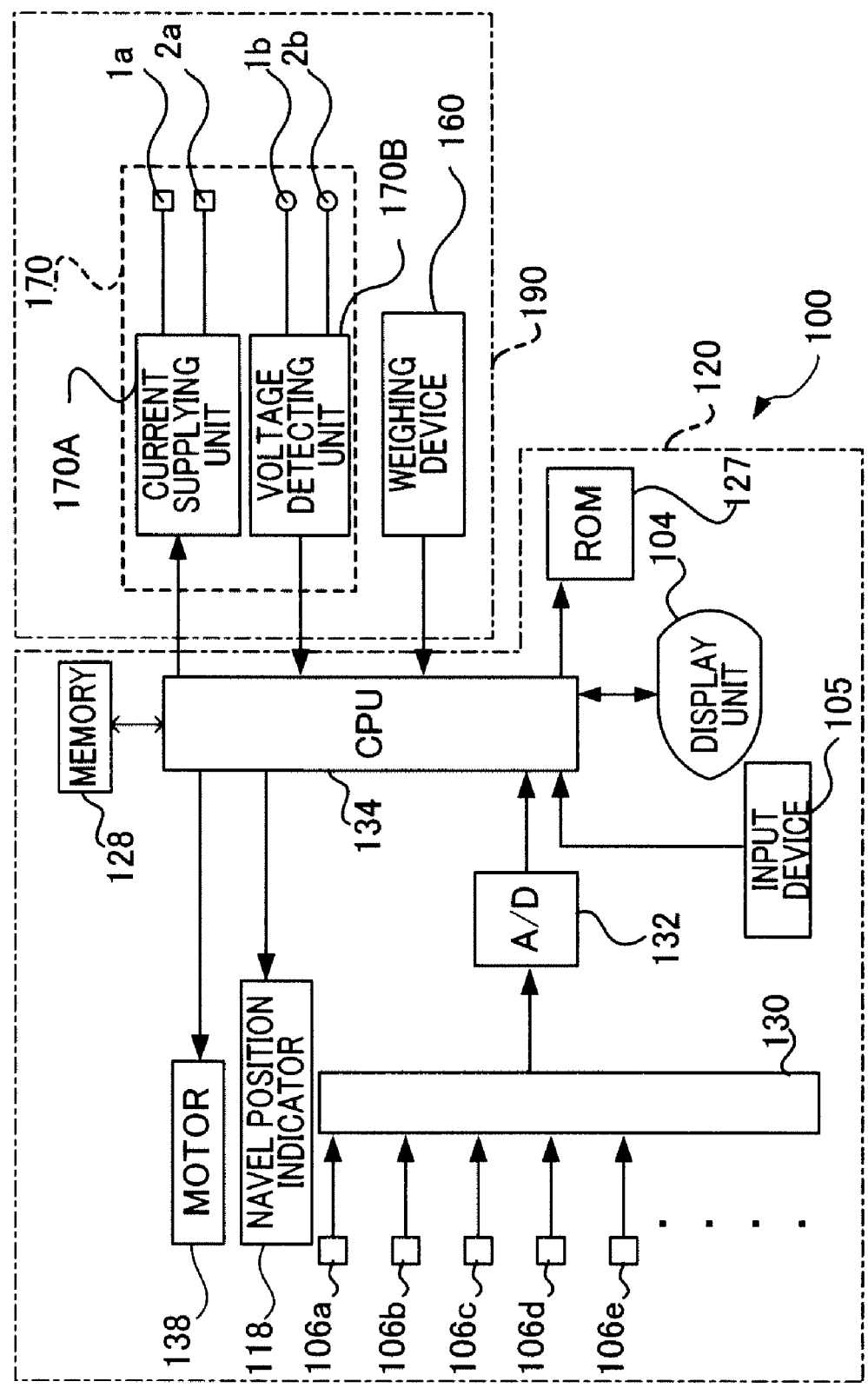
FIG. 4 is a block diagram showing an electrical configuration of body composition measuring apparatus 100.

As shown in FIG. 1, provided on the top surface of base plate unit 190 are current supply electrodes 1a and 2a and voltage detection electrodes 1b and 2b. Current supply electrodes 1a and 2a and voltage detection electrodes 1b and 2b are parts of bioelectrical impedance device 170 (FIG. 4).

Provided inside base plate unit 190 is a weight sensor (not shown). The weight sensor is capable of measuring the weight of human subject 10 when the human subject stands on base plate unit 190. The weight sensor is, for example, a load cell having a strip of metal fitted with strain gauges, and the load cell detects and outputs changes in voltage caused by strains of strain gauges. The weight sensor is a part of weighing device 160 (FIG. 4).

Frame 114 has a pair of parallel arms 103a and 103b extending horizontally and a connection member 102 of which both ends are connected to the arms 203a and 203b. One side of frame 114 is open so that human subject 10 can easily enter the interior area defined by frame 114 and can easily exit the frame. With this configuration, easy and speedy measurement is enabled.

Fixed to frame 114 is an attachment member 194 for attaching frame 114 to rod 192. Inside attachment member 194 is a frame level changer, although not shown, including a moving mechanism (for example, a ball screw or an endless belt) for moving frame 114 vertically with respect to rod 192 and a driving mechanism (for example, a motor 138) for driving the moving mechanism. Thus, rod 192 supports frame 114 so that frame 114 can slide along the medial line of human subject 10. Having this configuration, the apparatus can automatically and easily move frame 114 along the medial line of human subject 10 by means of the frame level changer.

A console 120 is attached to the upper end of rod 192. Provided on the top surface of console 120 are, as input devices to be operated by human subject 10 or an operator, an ON/OFF key 121, a Return key 122, a Move-Up key 123, and a Move-Down key 124. Furthermore, display unit 104 is provided on the top surface of console 120, with display unit 104 for displaying operation guidance, measurement results, or other information for human subject 10. Display unit 104 employs a touch panel input system and therefore serves also as an input device (height inputter, age inputter) for receiving input of parameters such as age and height. The information input by the input device is supplied to CPU 134.

It is to be noted that ON/OFF key 121, Return key 122, Move-Up key 123, and Move-Down key 124 may also serve as input devices (height inputter, age inputter) for receiving input of parameters such as age and height.

Figure 2:
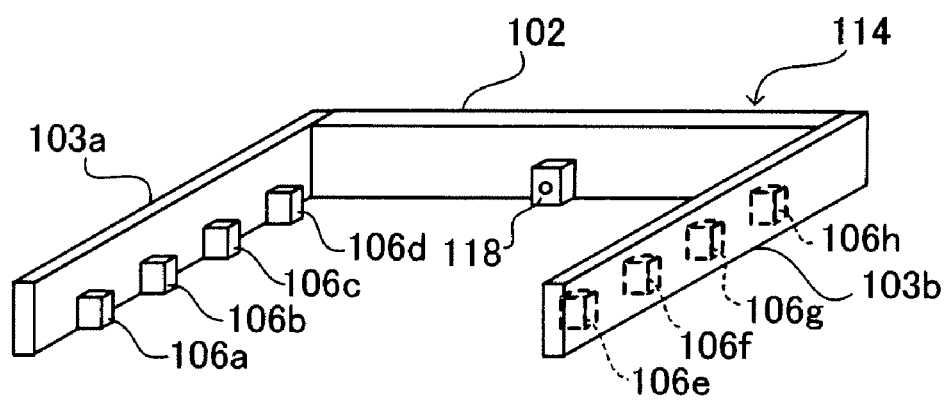
FIG. 2 is a perspective diagram showing an external view of a frame 114 of body composition measuring apparatus 100 of FIG. 1.
Figure 3:
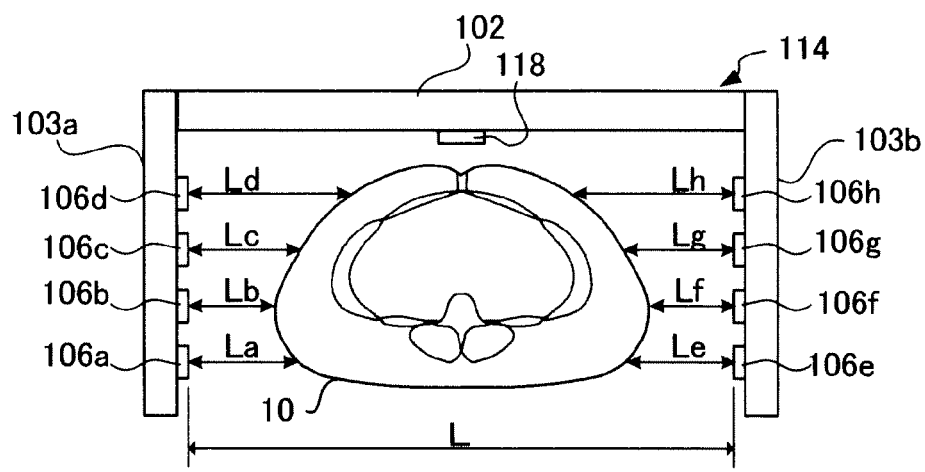
FIG. 3 is a horizontal section diagram showing a state in which frame 114 is set to the human subject.

FIG. 2 is a perspective diagram showing an external view of frame 114. FIG. 3 is a horizontal section diagram showing a state in which frame 114 is set to human subject 10. As shown in FIGS. 2 and 3, plural optical distance sensors (abdominal width distance measurers) 106 are disposed on the inner surface of frame 114. Sensors 106 are disposed on the same horizontal plane. In the figure, the appended letters "a" to "h" are used to distinguish each of the plural sensors 106. In the embodiment, eight sensors 106a to 106h are provided, but the number of sensors 106 is not limited to that shown in the embodiment. Estimating the abdominal width using more sensors 106 will yield a result that will have a higher correlation with the actual abdominal width. Therefore, a larger number of sensors 106 can be disposed as long as having that many sensors 106 does not make the configuration of the apparatus or an abdominal width calculating process too complicated.

Specifically, as shown in FIGS. 2 and 3, sensors 106a to 106d are disposed on the inner surface arm 103a of frame 114; and sensors 106e to 106h are disposed on the inner surface of arm 103b. Furthermore, the sensors 106a to 106d are spaced equally with respect to each other; and sensors 106e to 106h are spaced equally with respect to each other. However, sensors 106 may be disposed at variable intervals. For example, sensors 106 near the center to a long side of arms 103a and 103b may be disposed more densely than sensors 106 near the edges of arms 103a and 103b. The more sensors 106 are provided near the center of arms 103a and 103b, the higher the probability that the point to be measured will coincide with the most protruding portion of the abdomen of human subject 10. Therefore, a more accurate value of the abdominal width can be obtained.

Each sensor 106 has a light emitter for emitting a light such as an infrared light beam and has a light receiver for receiving the light reflected from whatever is in front of the sensor, such as human subject 10. The light receiver is an optical range finder and generates an electric signal corresponding to the distance from a position of the sensor to a position of whatever is directly in front of the sensor. The generated electric signal is supplied to CPU 134. Thus, each sensor measures the gap distance between the position of the sensor and a position of an object to be measured that is directly in front of the sensor.

More specifically, the light receiver of each sensor 106 receives a light reflected from a point at which the straight line in the direction of a distance measuring axis of the sensor intersects with an object. The light receiver generates an electric signal corresponding to the gap distance between the position of the point of the intersection and the position of the sensor. In this embodiment, the object to be measured is human subject 10, and the point of the intersection (i.e., the point to be measured) is a point on the surface of the body of human subject 10.

Specific examples are shown in FIG. 3. As shown in FIG. 3, the direction of the distance measuring axis of each sensor 106 is perpendicular to arms 103a and 103b and is in parallel with connection member 102. That is, in a case in which human subject 10 is in the interior area of frame 114, the direction of the distance measuring axis of each sensor 106 corresponds to the lateral direction (width direction) of the abdomen of human subject 10 standing on base plate unit 190. Therefore, a straight line connecting the sensor and the point to be measured is in parallel with the lateral direction of the abdomen of human subject 10. Sensor 106a receives a reflected light from the point to be measured to generate an electric signal corresponding to a gap distance La between sensor 106a and the point to be measured. Sensors 106b to 106h generate electric signals corresponding to gap distances Lb to Lh, respectively.

Sensors 106a to 106d mounted on arm 103a are disposed axisymmetrically with sensors 106e to 106h mounted on arm 103b, respectively, so that sensors 106a and 106e, sensors 106b and 106f, sensors 106c and 106g, sensors 106d and 106h each make up pairs. The distance measuring axes of the same pair are collinear. Thus, the members of each pair of sensors 106 face each other so as to sandwich the abdomen in its lateral direction. Furthermore, sensors 106a to 106d lie in a common straight line, as do sensors 106e to 106h. Therefore, the distances between sensors 106a and 106e, between sensors 106b and 106f, between sensors 106c and 106g, and between sensors 106d and 106h are the same, and each distance corresponds to the length "L" of FIG. 3. The plural pairs of sensors 106 measure gap distances at plural positions that are in parallel with the anteroposterior direction (i.e., the direction that is orthogonal to the abdominal width) of the abdomen of human subject 10.

A navel position indicator (navel position indicating means) 118 is mounted at the center between arms 103a and 103b of the connection member 102 of frame 114. Navel position indicator 118 is disposed on the same horizontal plane as are the sensors 106. In this embodiment, navel position indicator 118 is a light emitting device for emitting a beam of light (e.g., a laser pointer), but it is not limited thereto. The frame 114 is moved by the frame level changer and is brought to rest in a case in which navel position indicator 118 points to the navel position, i.e., a laser beam points at the navel of human subject 10. Positioning of frame 114 with respect to human subject 10 in this manner enables precise measurement of the abdominal width value without errors caused by mispositioning.

FIG. 4 is a block diagram showing an electric configuration of body composition measuring apparatus 100. Inside console 120 (FIG. 1) are a switch 130, an analog-to-digital (A/D) converter 132, a CPU (central processing unit) 134, a ROM (read only memory) 127, and a memory 128 as shown in FIG. 4. Switch 130 sequentially supplies output signals one by one from optical distance sensors 106a to 106h to A/D converter 132, and A/D converter 132 converts the supplied signals into digital signals. The digital signals output from A/D converter 132 are supplied to CPU 134. Accordingly, digital distance signals based on output signals of sensors 106a to 106h are sequentially supplied to CPU 134 one by one. Each of the digital distance signals represents a gap distance between a corresponding optical distance sensor 106 and a point to be measured on human subject 10 corresponding to the optical distance sensor 106, that is, gap distance La, Lb, Lc, Ld, Le, Lf, Lg, or Lh as shown in FIG. 3. Memory 128 is a volatile memory and is used as a work area for CPU 134, but it is not limited thereto. CPU 134 stores data of gap distances La, Lb, Lc, Ld, Le, Lf, Lg, and Lh represented by these distance signals in memory 128.

CPU 134 operates in accordance with a computer program or a computer program element stored in ROM 127. CPU 134 controls motor 138 (the driving mechanism) that drives the moving mechanism for moving frame 114 upward or downward, navel position indicator 118, and display unit 104. Furthermore, CPU 134 executes an operation in accordance with a signal from an input device 105 including manual interfaces such as ON/OFF key 121, Return key 122, Move-Up key 123, and Move-Down key 124 and from the touch panel of display device 104.

Additionally, CPU 134 serves as a calculator (calculation means) for calculating the abdominal width based on data of gap distances once stored in memory 128 in accordance with equations stored in ROM 127. There is further stored in ROM 127 visceral fat area calculating equations for calculating visceral fat area based on the abdominal width, weight measured by weighing device 160, and foot-to-foot bioelectrical impedance measured by bioelectrical impedance device 170. Thus, CPU 134 serves as a calculator for calculating visceral fat area based on the abdominal width distance, weight, bioelectrical impedance, and the equations.

CPU 134 may be realized physically by plural central processing units. Alternatively, they may be realized functionally by a computer program that is executed by a single central processing unit.

Inside base plate unit 190 of FIG. 1 are bioelectrical impedance device 170 (a current supplying unit 170A and a voltage detecting unit 170B) and weighing device 160 shown in FIG. 4. Current supplying unit 170A of bioelectrical impedance device 170, when human subject 10 stands on base plate unit 190, applies high-frequency constant microcurrent to the sole of each foot of human subject 10 through current supply electrodes 1a and 2a that have been formed on base plate unit 190, and voltage detecting unit 170B measures a potential difference between voltage detection electrodes 1b and 2b. Weighing device 160, when human subject 10 stands on base plate unit 190, uses the above-described weight sensor to measure the weight of human subject 10. Bioelectrical impedance device 170 and weighing device 160 are connected to CPU 134.

Figure 5:
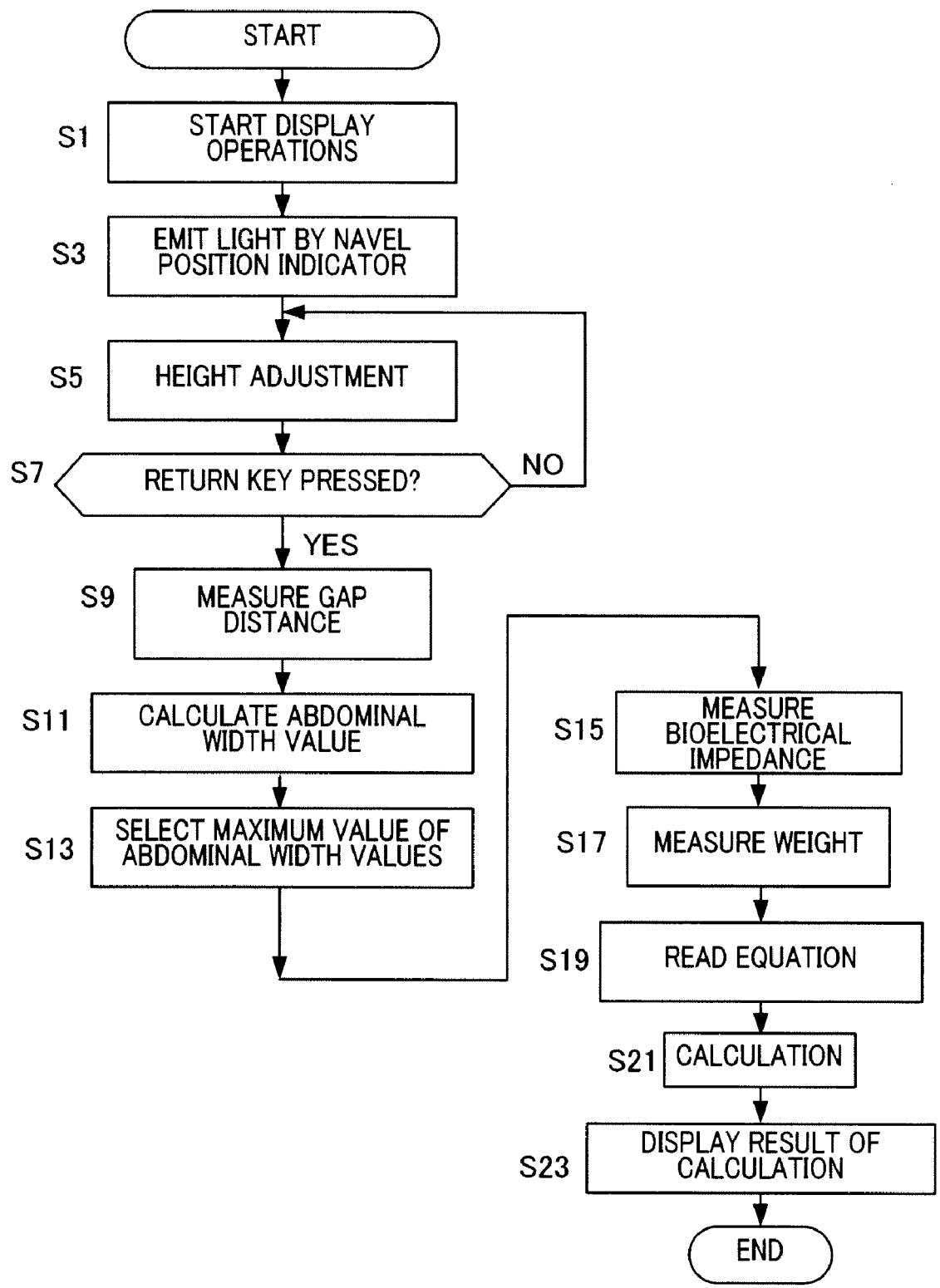
FIG. 5 is a flowchart showing use and operations of body composition measuring apparatus 100.

FIG. 5 is a flowchart showing a flow of a calculation process of body composition measuring apparatus 100. There is stored in ROM 127 a computer program or a computer program element corresponding to the flowchart, and CPU 134 operates in accordance with the computer program or the computer program element. In this embodiment, ROM 127 is used as a recording medium that has stored the computer program or the computer program element, but a hard disk, compact disk, digital versatile disk, flexible disk, or any other recording medium that is suitable may be used for this purpose.

The operation shown in FIG. 5 is started in a case in which ON/OFF key 121 of FIG. 1 is pressed. In Step S1, CPU 134 drives display unit 104 to start display operations at display unit 104. CPU 134 then displays a guide message for prompting human subject 10 to stand on base plate unit 190 at a position suitable for measurement on display unit 104. Such a message may be, for example, "Stand on the base plate unit and align your toes on the reference line". Human subject 10 is thus prompted to align the toes on reference line 196 (FIG. 1).

Subsequently in Step S3, CPU 134 drives navel position indicator 118 so that it starts emitting light, and in Step S5, CPU 134 adjusts the height (vertical position) of navel position indicator 118. In the height adjustment, CPU 134 displays on display unit 104 a guide message such as "Operate the Move-Up key or the Move-Down key so that the light is irradiated onto your navel". This guide message is for prompting human subject 10 to press at least one of Move-Up key 123 and Move-Down key 124 (FIG. 1) so that the beam of light emitted from navel position indicator 118 irradiates the navel of human subject 10. When Move-Up key 123 is pressed, Move-Up key 123 gives a move-up command to CPU 134. In the height adjustment, CPU 134 drives motor 138 to raise frame 114 while the move-up command is being given. When Move-Down key 124 is pressed, Move-Down key 124 gives a move-down command to CPU 134. In the height adjustment, CPU 134 drives motor 138 to lower frame 114 while the move-down command is being given.

The height adjustment process continues until Return key 122 is pressed (Step S7). In a case in which Return key 122 is pressed, CPU 134 causes navel position indicator 118 to stop emitting and also causes display unit 104 to display a guide message (for example, "Measurement in progress") to indicate that the measurement of the abdominal width is in progress. After this, CPU 134 no longer drives motor 138, even in a case in which Move-Up key 123 or Move-Down key 124 is pressed.

In Step S9, CPU 134 gives sensors 106a to 106h a drive command to drive each sensor 106. In a case in which digital distance signals are input from A/D converter 132, CPU 134 stores in memory 128 data showing gap distance values represented by the digital distance signals. Thus, the gap distance between each sensor 106 and the point to be measured is obtained.

In Step S11, CPU 134 serves as a calculator (calculating means) that calculates candidate values of the abdominal width based on the data of gap distance once stored in memory 128. In this embodiment, four values of the abdominal width are computed in Step S11 as candidate abdominal width values X1 through X4, with the four values being computed in accordance with the following Equations (A) to (D):

$$X1 = L - (La + Le) \quad \text{Equation (A)}$$

$$X2 = L - (Lb + Lf) \quad \text{Equation (B)}$$

$$X3 = L - (Lc + Lg) \quad \text{Equation (C)}$$

$$X4 = L - (Ld + Lh) \quad \text{Equation (D)}$$

As is obvious from FIG. 3, the four candidate abdominal width values X1 to X4 each indicate the abdominal width. In Step S13, CPU 134 selects, from among the candidate abdominal width values X1 to X4, the maximum value, i.e., the maximum distance in the lateral direction of the abdomen, as the abdominal width.

Subsequently, in Step S15, CPU 134 obtains a measured value of foot-to-foot bioelectrical impedance of human subject 10 from bioelectrical impedance device 170, and in Step S17 obtains from weighing device 160 a measured value of weight. Then in Step S19, CPU 134 reads from ROM 127 the visceral fat area calculating equation for calculating visceral fat area.

The calculating equation is derived from a multiple regression analysis and is expressed as the following estimation equation (1).

$$Y = k1 + k2*X + k3*W + k4*\%\text{FAT} \quad \text{Equation (1)}$$

in which Y is visceral fat area, X is the abdominal width, W is weight, % FAT is body fat ratio, and k1 to k4 are constants (coefficients) that are determined as appropriate through multiple regression analysis.

Furthermore, CPU 134 estimates body fat ratio % Fat in accordance with the following Equation (2).

$$\%\text{Fat} = f1*Z*W/H^2 - f2 \quad \text{Equation (2)}$$

in which f1 and f2 are constants and are values determined as appropriate through multiple regression analysis, Z is bioelectrical impedance, and H is height. The height H is a parameter for generating body fat ratio % Fat and is input from the touch panel of display unit 104 by human subject 10 or by an operator.

In the first term of Equation (2), "$W/H^2$" is a body mass index BMI and indicates the degree of obesity. The constants f1 and f2 of Equation (2) are derived by performing multiple regression analysis on a body fat ratio obtained using a DXA method (Dual energy X-ray Absorptiometry method). The DXA method uses two types of X-ray beams with different wavelengths to obtain body composition of humans based on the amount of transmitted light. The DXA method is capable of measuring body fat ratio with high accuracy, but it requires a large device, and human subject 10 is inevitably exposed to radiation, although the amount of radiation is very small. However, according to the bioelectrical impedance method used in the present embodiment, an easy and safe estimation of body fat ratio % Fat is made possible.

In a conventional method, the abdominal size is not used as a parameter for estimating visceral fat area, but visceral fat area is estimated based on BMI ($W/H^2$), age, and body fat mass (body fat ratio) estimated using the bioelectrical impedance method.

Figure 6:
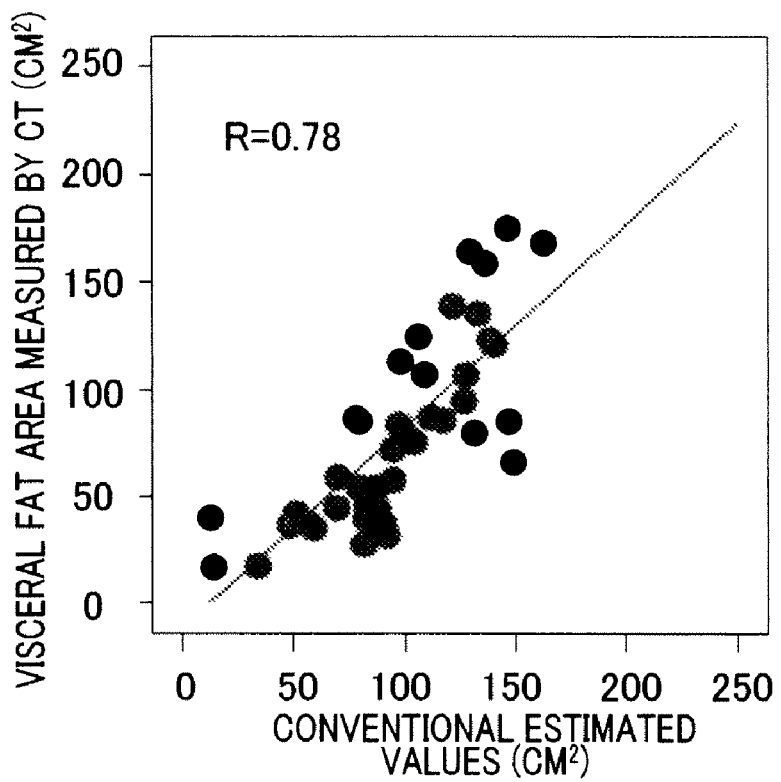
FIG. 6 is a scatter diagram showing a relationship between estimated values of visceral fat area estimated by a conventional method and values of visceral fat area actually measured by a CT (computerized axial tomography) scanning method.
Figure 7:
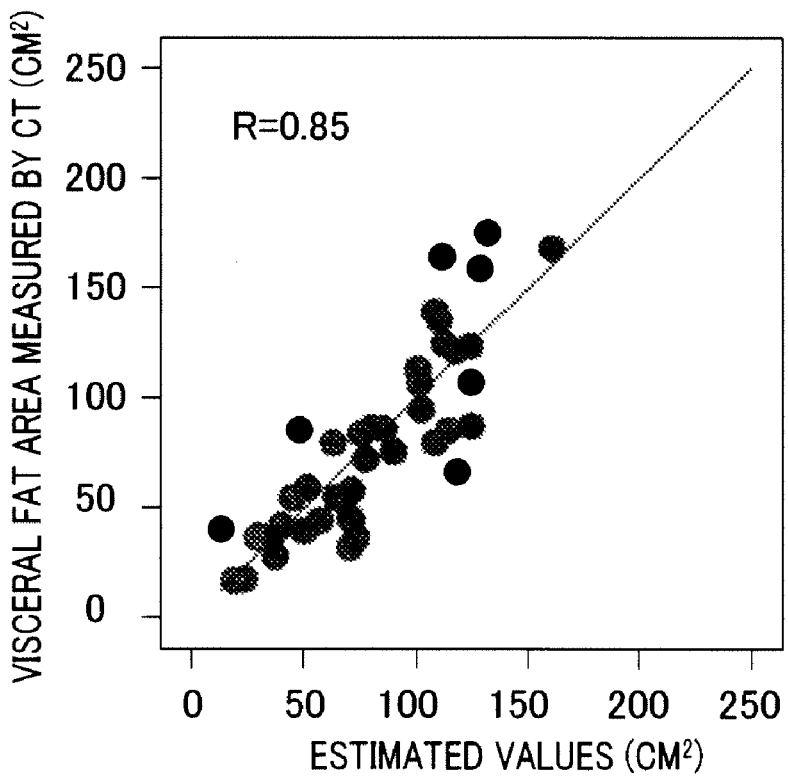
FIG. 7 is a scatter diagram showing a relationship between estimated values of visceral fat area estimated based on the abdominal size and values of visceral fat area actually measured by a CT scanning method.

FIG. 6 is a scatter diagram showing a relationship between estimated values of visceral fat area estimated by the conventional method and values of visceral fat area actually measured by a CT scanning method. FIG. 7 is a scatter diagram showing a relationship between estimated values and actual values in a case in which the estimation of visceral fat area is performed using the abdominal size as an argument. As shown in FIGS. 6 and 7, the higher correlation between estimated values and actual values is observed in a case in which the abdominal size is used as a parameter than in a conventional method in which the abdominal size is not used in estimation, as indicated by R (correlation coefficient), which is 0.78 in FIG. 6, and by R, which is 0.85 in FIG. 7. Therefore, estimating visceral fat area based on an estimation equation using the abdominal size as a parameter can yield estimation results with higher accuracy. Thus, according to Equation (1) used in the present embodiment, estimation with higher accuracy is enabled compared with the estimation using the conventional method.

Additionally, according to the present embodiment, because the abdominal width is measured by a distance sensor, the abdominal size can be estimated more accurately compared with a case in which human subject 10 or an operator manually inputs an abdominal size that is already known to human subject 10 or measures the abdominal circumference using a measuring instrument such as a tape measure. Therefore, the accuracy in estimating visceral fat area is greatly enhanced.

In Step S21 of FIG. 5, CPU 134 serves as a calculator (calculating means) that calculates body fat ratio % Fat based on the above Equation (2), height H, bioelectrical impedance Z obtained in Step S15, and weight W obtained in Step S17, and then calculates (estimates) visceral fat area Y based on the above Equation (1), the abdominal width X obtained in Step S13, weight W obtained in Step S17, and body fat ratio % Fat. Subsequently, in Step S23, CPU 134 displays the estimated value of visceral fat area on display unit 104 to end the operation.

Modification 1:

In the above embodiment, abdominal width X, weight W, foot-to-foot bioelectrical impedance Z, and height H are used as parameters in Equations (1) and (2) by which visceral fat area is estimated. However, according to the following Equation (3), visceral fat area can be estimated without using height H as a parameter if body density BD is employed as a parameter.

Equation (3) is derived from multiple regression analysis and is expressed as a multiple regression equation as follows:

$$Y = p1*Age + p2*X + p3*W*Z/\{a*W/X^2\}^2 + p4 \qquad \text{Equation (3)}$$

in which Y is visceral fat area, Age is age, X is abdominal width, W is weight, Z is bioelectrical impedance, "a" and "p1" to "p4" are constants (coefficients) that are determined as appropriate through the multiple regression analysis, and "$W*Z/\{a \times W/X^2\}^2$" is body density BD.

The following is a principle based on which visceral fat area can be estimated based on body density BD.

If it is assumed that a human body approximates a column of which a length (height) H is unknown and volume V and diameter D are known, the length H can be obtained in accordance with $H = V/D^2$. If D is assumed to be a diameter of a particular portion of a human body, diameter D can be considered as being abdominal width (i.e., diameter D≈abdominal width X). Furthermore, if the specific gravity of the tissues of the human body is assumed as being similar to that of water, we can assume that weight W≈volume V. The following equation is derived as a result.

$$H = a*W/X^2 \qquad \text{Equation (4)}$$

Body density BD is the ratio of weight to the volume of the whole body. Because the volume of a body of water can be obtained by the bioelectrical impedance method, the following equation (Equation (5)) will be derived through multiple regression analysis based on body density BD actually measured, for example by a body water weight scale and the volume of body water obtained by the bioelectrical impedance method.

$$\text{Body Density } BD = W*Z/H^2 \qquad \text{Equation (5)}$$

Substitution of Equation (4) into Equation (5) yields the following equation.

$$BD = W*Z/(a*W/X^2)^2 \qquad \text{Equation (6)}$$

Therefore, based on Equations (3) and (6), the following equation will be derived through multiple regression analysis.

$$Y = p1*Age + p2*X + p3*BD + p4 \qquad \text{Equation (7)}$$

in which p1 to p4 are constants that are determined as appropriate through multiple regression analysis.

According to Equations (3) and (7), visceral fat area increases as age increases, abdominal width increases, and body density increases.

Figure 8:
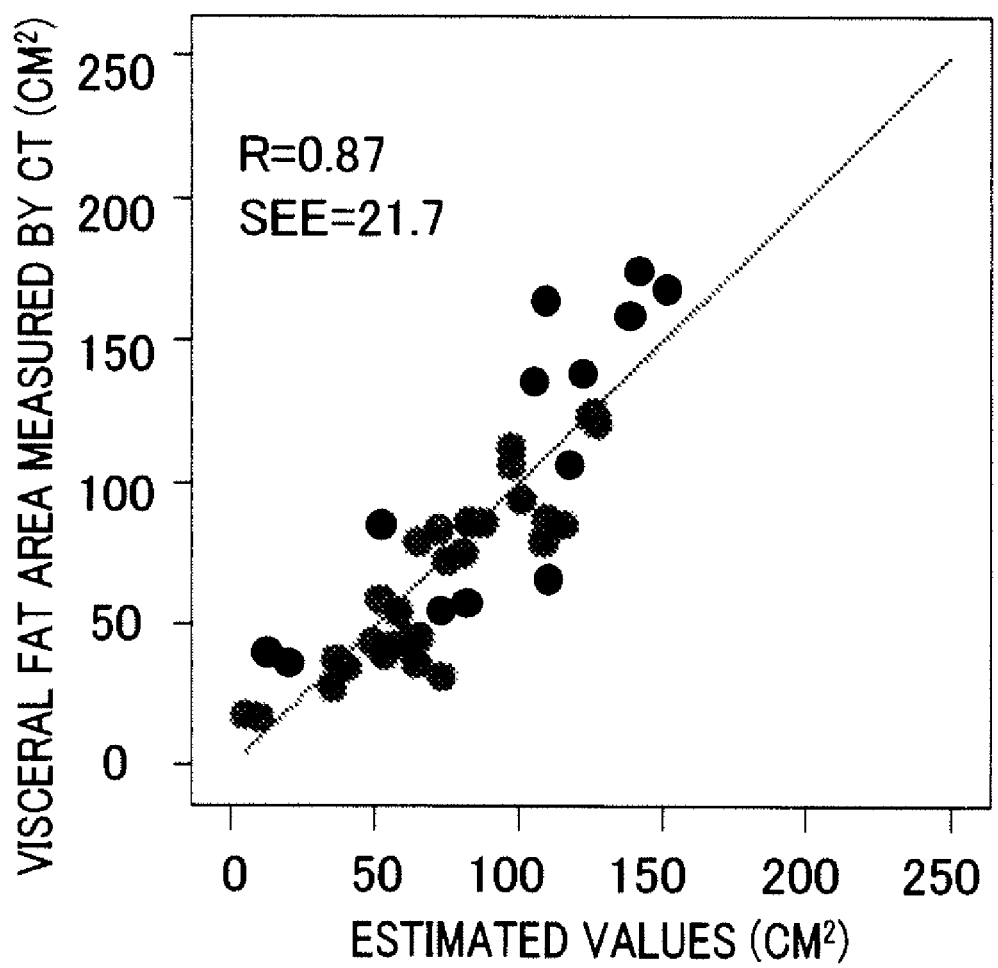
FIG. 8 relates to a modification and is a scatter diagram showing a relationship between estimated values of visceral fat area estimated based on abdominal size and values of visceral fat area actually measured by a CT scanning method.

FIG. 8 is a scatter diagram showing a relationship between estimated values of visceral fat area obtained in accordance with Equation (3) and actual values of visceral fat area measured by the CT scanning method. As shown in FIG. 8, the standard error estimation (SEE) is 21.7 cm$^2$, that is, estimated values obtained in accordance with Equation (3) fall within 21.7 cm$^2$ error, and R is 0.87. Thus, the correlation between estimated values and actual values of visceral fat area is high because the correlation coefficient is higher than that of the conventional method (FIG. 6). Thus, accurate estimation is enabled if the estimation is performed in accordance with Equation (3) since the abdominal size is used as a parameter. Furthermore, height H need not be used in estimating visceral fat area as a parameter according to this modification.

Furthermore, in the above embodiment, body fat ratio % FAT is estimated based on weight W, height H, and bioelectrical impedance Z, and visceral fat area Y is calculated in accordance with Equation (1), $Y = k1 + k2*X + k3*W + k4*\%$ FAT. However, height H need not be used as a parameter if the body density BD is employed to obtain body fat ratio % FAT. Specifically, body density BD is obtained based on weight W, abdominal width X, bioelectrical impedance Z, and Equation (6) as described above, and the thus-obtained body density BD is assigned to an equation, body fat ratio % FAT=[(q1/BD)−q2]*100 (Brozek's equation, in which q1 and q2 are coefficients), to obtain body fat ratio % FAT. The thus-obtained body fat ratio % FAT is assigned to Equation (1) together with weight W and abdominal width X to calculate visceral fat area. According to this modification, a visceral fat area can be computed based simply on weight W, abdominal width X, and bioelectrical impedance Z. Because weight W, abdominal width X, and bioelectrical impedance Z are measured by body composition measuring apparatus 100, no parameters need to be input by human subject 10 or an operator. Therefore, the convenience is greatly enhanced.

Modification 2:

In the above embodiment, plural pairs of sensors 106 are fixedly disposed on frame 114 at plural positions that are in parallel with the anteroposterior direction of the abdomen, with sensors of the same pair facing each other, and the maximum value is selected as the abdominal width from among the candidate abdominal width values obtained based on measurements by each pair. However, in this case, the positions of a pair of sensors 106 that have measured gap distances corresponding to the selected maximum value do not always correspond to the locations at which the abdomen is protruding the most at the sides of human subject 10. Specifically, as shown in the example of FIG. 3, the abdominal width value obtained based on the measurements by sensors 106b and 106f is likely to be selected as the maximum abdominal width, but the selected value might not be the abdominal width value of the most protruding portion of the abdomen. Accordingly, two movable sensors 106 may be provided on arms 103a and 103b instead of plural pairs of sensors 106. These two sensors 106 are arranged respectively on arms 103a and 103b so that a straight line connecting the sensors is in parallel with the lateral direction of the abdomen and is on the same horizontal plane. The sensors 106 are movable in the anteroposterior direction of the abdomen (a direction orthogonal to the lateral direction of the abdomen) while the straight line connecting the sensors is maintained in parallel with respect to the lateral direction of the abdomen. A driving mechanism (not shown) moves the two sensors 106 synchronously, and measurement of gap distance between a sensor position and a measured position is performed, for example, at regular distance intervals while moving. In this case, CPU 134 computes plural candidate values of the abdominal width based on measured gap distance values and determines the maximum abdominal width value as the abdominal width X. Alternatively, two sensors (e.g., 106a and 106e), respectively disposed on arms 103a and 103e, may move independently of each other at different timings, but the distance intervals of measurements for sensor 106a may be the same as those for sensor 106e so that the measurement lines of sensor 106a at plural measurement positions coincide with the measurement lines of sensor 106e at plural measurement positions.

In another alternative, because the human body is bilaterally symmetrical, a single sensor (e.g., 106a or 106e), instead of the two sensors 106a and 106e, may be disposed on one of the arms 103a and 103b, so that the sensor is caused to move along arm 103a or 103b. In this case, CPU 134 doubles the gap distance value measured by sensor 106 and deducts the doubled gap distance value from the distance L (FIG. 3) to obtain a candidate value of abdominal width.

Furthermore, CPU 134 may obtain coordinates constituting an outer rim of the abdomen based on gap distances detected by the sensors as used in the above embodiment and in the above modification, executes curved interpolation based on the coordinates, to obtain the outer rim of the abdomen, based on which two coordinates having a maximum distance therebetween in the lateral direction of the abdomen is output as the abdominal width. However, in this case, the independently movable sensors of the same pair do not necessarily perform measurements at the same distance intervals.

Other Modifications:

In the above embodiment, visceral fat area is estimated based on the measured abdominal width, but the present invention is not so limited. Other types of body composition indices (body fat ratio, fat ratio of the trunk portion, fat area of the abdomen, abdominal subcutaneous fat thickness, abdominal muscle thickness, abdominal subcutaneous fat area, and similar indices) can be estimated based on the abdominal width.

In the above embodiment, a body composition index is computed based on the measured abdominal width. However, abdominal circumference (for example, waist circumference) may be estimated based on the measured abdominal width and data on correlations between the abdominal width values and abdominal circumference values. In this case, a body composition index may be computed based on the estimated abdominal circumference.

In the above-described embodiment, for determining the abdominal width, sensors 106 are mounted in the horizontal plane that passes through the navel of human subject 10 and is vertical to the median line of human subject 10. However, by adjusting the location of the navel position indicator 118 relative to the sensors 106, the sensors 106 may be mounted in another horizontal plane vertical to the median line of the human subject 14 for determining the abdominal width.

Although in the above-described embodiments display unit 104 is used as an output device to which the measurement result is output, the apparatus may output the measurement result in any other suitable manner. For example, the apparatus may include a printer for printing out the measurement result. The apparatus may send, or may store, or may both send and store, measurement result signals indicating the measurement result to an outside device.

Although the present invention has been illustrated and described with reference to preferred embodiments thereof, it will be understood by those skilled in the art that various changes in structure and details may be made thereto without departing from the spirit and scope of the invention as defined by the claims. Such variations, alterations, and modifications are intended to be encompassed in the scope of the present invention.

What is claimed is:

1. A body composition measuring apparatus, for estimating a body composition index including visceral fat area, comprising:
    a bioelectrical impedance measurer that measures foot-to-foot bioelectrical impedance by applying at least one electrode to the sole of each foot of a human subject;
    an abdominal width measurer that measures an abdominal width of the human subject that uses a reflection-type contactless distance measuring sensor to measure the abdominal width, the contactless distance measuring sensor measuring a gap distance between a position of the sensor and a position of a point to be measured, with a distance measuring axis of the contactless distance measuring sensor being in parallel with a lateral direction of the abdomen;
    a frame including a navel position indicator that indicates the position of a navel of the human subject,
    wherein the frame is brought to rest at a position at which the navel of the human subject is indicated by the navel position indicator,
    wherein the abdominal width measurer measures the abdominal width at the position at which the navel position of the human subject is indicated;
    a weigher that measures a body weight of the human subject; and
    a calculator having memory with a computer program stored thereon, said calculator: determining body fat ratio based on bioelectrical impedance and weight; determining a body composition index including visceral fat area by performing certain calculations using the measured abdominal width, weight, bioelectrical impedance, and body fat ratio derived from the bioelectrical impedance and weight; and displaying the visceral fat area of the subject.

2. A body composition measuring apparatus according to claim 1, further comprising a height inputter that receives input of the height of the human subject,
    wherein the calculator uses the height received by the height inputter in addition to the abdominal width, the weight, and the foot-to-foot bioelectrical impedance to estimate the body composition index.

3. A body composition apparatus according to claim 2, wherein the calculator further uses height in calculating the body fat ratio.

4. A body composition measuring apparatus according to claim 1, further comprising an age inputter that receives input of the age of the human subject,
    wherein the calculator concurrently serves as a body density estimator that estimates body density based on the abdominal width, the weight, and the foot-to-foot bioelectrical impedance, and the calculator calculates the body composition index based on the abdominal width, the body density, and the age input by the age inputter.

5. A body composition measuring apparatus according to claim 1,
    wherein the abdominal width measurer comprises:
    at least a pair of contactless distance measuring sensors, each sensor including a light emitter and a light receiver; and
    the at least pair of contactless distance measuring sensors being arranged on the frame so that the pair of sensors are facing each other and are sandwiching the abdomen in parallel in a lateral direction of the abdomen, with a straight line connecting the pair of sensors corresponding to the distance measuring axis of each of the pair, and the pair of sensors measuring the gap distance at plural positions that are in parallel with an anteroposterior direction of the abdomen, wherein the abdominal width measurer executes a predetermined calculation on plural gap distances measured at the plural positions to output a result of the calculation as the abdominal width.

6. A body composition measuring apparatus according to claim 5, wherein a side of the frame is open so that a human subject can enter the interior area of the frame.

7. A body composition measuring apparatus according to claim 5, wherein the navel position indicator is a light emitting device for emitting a beam of light;

wherein the apparatus further comprises a rod for supporting the frame so that the frame can slide along a medial line of the standing human subject and a frame level changer for changing a level of the frame along the rod; and wherein the abdominal width measurer measures the abdominal width when the frame is stopped.

8. A body composition measuring apparatus according to claim 7, further comprising a height inputter that receives input of the height of the human subject, wherein the calculator uses the height received by the height inputter in addition to the abdominal width, the weight, and the foot-to-foot bioelectrical impedance to estimate the body composition index.

9. A body composition measuring apparatus according to claim 7, further comprising an age inputter that receives input of the age of the human subject, wherein the calculator concurrently serves as a body density estimator that estimates body density based on the abdominal width, the weight, and the foot-to-foot bioelectrical impedance, and the calculator calculates the body composition index based on the abdominal width, the body density, and the age input by the age inputter.

10. A body composition measuring apparatus according to claim 5, wherein the distance between the pair of contactless distance measuring sensors facing each other is a predetermined length, the pair of contactless measuring sensors including at least a pair of a first sensor and a second sensor; and wherein the abdominal width is obtained by deducting the gap distance measured by the first sensor and the gap distance measured by the second sensor from the predetermined length.

11. A body composition measuring apparatus according to claim 10, wherein the first sensor and the second sensor are movable in the anteroposterior direction of the abdomen while maintaining the straight line connecting the first and the second sensors in parallel with the lateral direction of the abdomen.

12. A body composition measuring apparatus according to claim 10, wherein the naval position indicator is a light emitting device for emitting a beam of light;

wherein the apparatus further comprises a rod for supporting the frame so that the frame can slide along a medial line of the standing human subject and a frame level changer for changing a level of the frame along the rod; and wherein the abdominal width measurer measures the abdominal width when the frame is stopped.

13. A body composition measuring apparatus according to claim 1, wherein the abdominal width measurer further comprises two contactless distance measuring sensors facing each other that are arranged on the frame so that the sensors move in the anteroposterior direction of the abdominal width independently of each other to measure gap distances at plural positions that are in parallel with an anteroposterior direction of the abdomen, each sensor including a light emitter and a light receiver, and wherein the abdominal width measurer executes a predetermined calculation on the plural gap distances measured at the plural positions to output a result of the calculation as the abdominal width.

14. A body composition measuring apparatus according to claim 13, wherein a side of the frame is open so that a human subject can enter the interior area of the frame.

15. A body composition measuring apparatus according to claim 13, wherein the navel position indicator is a light emitting device for emitting a beam of light;

wherein the apparatus further comprises a rod for supporting the frame so that the frame can slide along a medial line of the standing human subject and a frame level changer for changing a level of the frame along the rod; and wherein the abdominal width measurer measures the abdominal width when the frame is stopped.

16. A body composition measuring apparatus according to claim 15, further comprising a height inputter that receives input of the height of the human subject, wherein the calculator uses the height received by the height inputter in addition to the abdominal width, the weight, and the foot-to-foot bioelectrical impedance to estimate the body composition index.

17. A body composition measuring apparatus according to claim 15, further comprising an age inputter that receives input of the age of the human subject, wherein the calculator concurrently serves as a body density estimator that estimates body density based on the abdominal width, the weight, and the foot-to-foot bioelectrical impedance, and the calculator calculates the body composition index based on the abdominal width, the body density, and the age input by the age inputter.

18. A body composition measuring apparatus according to claim 1, wherein the body composition index further includes at least one selected from the group consisting of fat ratio of the trunk portion, total fat area of the abdomen, abdominal subcutaneous fat thickness, abdominal muscle thickness, and abdominal subcutaneous fat area.

* * * * *